United States Patent
Hagen

(10) Patent No.: US 11,206,872 B2
(45) Date of Patent: Dec. 28, 2021

(54) STABLE-FOAM DISPENSING DEVICE AND CARTRIDGE

(71) Applicant: ConsumerNext Labs GmbH, Lower Saxony (DE)

(72) Inventor: Klaus Hagen, Lower Saxony (DE)

(73) Assignee: ConsumerNext Labs GmbH, Haren (DE)

( * ) Notice: Subject to any disclaimer, the term of this patent is extended or adjusted under 35 U.S.C. 154(b) by 0 days.

(21) Appl. No.: 16/887,239

(22) Filed: May 29, 2020

(65) Prior Publication Data

US 2021/0307411 A1    Oct. 7, 2021

(30) Foreign Application Priority Data

Apr. 7, 2020 (GB) ....................................... 2005160
May 28, 2020 (EP) ....................................... 20177196

(51) Int. Cl.
*A24F 42/20* (2020.01)
*A61M 15/00* (2006.01)
(Continued)

(52) U.S. Cl.
CPC .............. *A24F 42/20* (2020.01); *A24F 42/60* (2020.01); *A61J 7/0053* (2013.01);
(Continued)

(58) Field of Classification Search
CPC . A61K 8/046; A61M 31/002; A61M 15/0013; A61M 15/0093;
(Continued)

(56) References Cited

U.S. PATENT DOCUMENTS 3,410,279 A    11/1968 Moshy et al.
4,002,178 A    1/1977 Fiore et al.
(Continued)

FOREIGN PATENT DOCUMENTS

AU         721146     10/1998
AU       2015332008    4/2016
(Continued)

OTHER PUBLICATIONS

Japanese Office Action in JP App. No. 2020-097724 dated Aug. 14, 2020.
(Continued)

*Primary Examiner* — Kevin C Sirmons
*Assistant Examiner* — Alexandra Lalonde
(74) *Attorney, Agent, or Firm* — Nixon Peabody LLP; Jeffrey L. Costellia

(57) ABSTRACT

A stable-foam inhalation-device cartridge for a stable-foam inhalation device which dispenses a stable foam to be consumed by a user. The cartridge is devoid of an electrical energisation component. The cartridge includes a flexible mixing chamber, first and second foam-generation elements, an expansion chamber, a partitioning element having one or more mixing members for agitating a consumable foam and a discharge element. The discharge element has an outlet opening an inlet opening and a discharge conduit which interconnects the inlet opening with the outlet opening. The discharge conduit has a longitudinal extent which locates the inlet opening at a position closer to the partitioning element than to the outlet opening.

19 Claims, 8 Drawing Sheets

(51) Int. Cl.
  *A24F 42/60* (2020.01)
  *A61J 7/00* (2006.01)

(52) U.S. Cl.
  CPC ..... *A61M 15/0005* (2014.02); *A61M 2205/13* (2013.01); *A61M 2205/3344* (2013.01); *A61M 2205/587* (2013.01)

(58) Field of Classification Search
  CPC .... A61M 2039/066; A61M 2039/0673; B05B 7/04; B05B 7/0483; A61J 7/0053
  See application file for complete search history.

(56) References Cited

U.S. PATENT DOCUMENTS

| | | |
|---|---|---|
| 4,724,615 A | 2/1988 | Mackles et al. |
| 5,215,221 A | 6/1993 | Dirksing |
| 5,249,586 A | 10/1993 | Morgan et al. |
| 5,865,186 A | 2/1999 | Volsey, II |
| 6,062,213 A | 5/2000 | Fuisz et al. |
| 6,461,592 B1 | 10/2002 | Chang et al. |
| 6,481,435 B2 | 11/2002 | Hochrainer et al. |
| 6,626,379 B1 | 9/2003 | Ritsche et al. |
| 6,986,346 B2 | 1/2006 | Hochrainer et al. |
| 7,040,311 B2 | 5/2006 | Hochrainer et al. |
| 7,213,593 B2 | 5/2007 | Hochrainer |
| 7,500,485 B1 | 3/2009 | Shepard et al. |
| 7,793,655 B2 | 9/2010 | Hochrainer |
| 7,938,125 B2 | 5/2011 | John et al. |
| 7,980,243 B2 | 7/2011 | Hochrainer |
| 8,424,541 B2 | 4/2013 | Crawford et al. |
| 8,464,706 B2 | 6/2013 | Crockford et al. |
| 8,695,587 B2 | 4/2014 | Imran |
| 8,701,679 B2 | 4/2014 | Crawford et al. |
| 8,820,316 B2 | 9/2014 | Crockford et al. |
| 9,463,291 B2 | 10/2016 | Imran |
| 9,657,324 B1 | 5/2017 | Kondo et al. |
| 10,052,443 B2 | 8/2018 | Hazani |
| 10,092,700 B2 | 10/2018 | Norebring |
| 10,149,850 B2 | 12/2018 | Mishra et al. |
| 10,188,823 B2 | 1/2019 | Srinivasan et al. |
| 10,307,551 B2 | 6/2019 | Imran |
| 10,327,468 B2 | 6/2019 | Scholl |
| 10,369,301 B2 | 8/2019 | Hazani |
| 10,391,069 B2 | 8/2019 | Gogova et al. |
| 10,406,299 B2 | 9/2019 | Seguin et al. |
| 10,406,300 B2 | 9/2019 | Seguin et al. |
| 10,874,134 B2 | 12/2020 | Sutton |
| 10,881,132 B2 | 1/2021 | Mua et al. |
| 10,973,996 B2 | 4/2021 | Nagar |
| 10,994,081 B2 | 5/2021 | Chen et al. |
| 2007/0256688 A1 | 11/2007 | Schuster et al. |
| 2011/0088708 A1 | 4/2011 | John et al. |
| 2011/0183057 A1 | 7/2011 | Jones et al. |
| 2011/0209700 A1* | 9/2011 | Kreutzmann ..... A61M 15/0021 128/200.14 |
| 2012/0055494 A1 | 3/2012 | Hunt et al. |
| 2012/0167902 A1 | 7/2012 | Macko et al. |
| 2013/0056005 A1 | 3/2013 | Knudsen |
| 2013/0236605 A1 | 9/2013 | Crawford et al. |
| 2014/0088486 A1* | 3/2014 | Uhland .................. A61M 5/19 604/20 |
| 2016/0165953 A1 | 6/2016 | Goode, Jr. |
| 2016/0286851 A1 | 10/2016 | Hufnagel et al. |
| 2018/0272367 A1* | 9/2018 | Rayner .................... B05B 7/04 |
| 2019/0099566 A1* | 4/2019 | Gramann ............. A61M 15/02 |
| 2019/0175498 A1 | 6/2019 | Gao et al. |
| 2019/0182909 A1 | 6/2019 | Fursa et al. |
| 2019/0200667 A1 | 7/2019 | Phililps et al. |
| 2019/0328040 A1 | 10/2019 | Turbi |
| 2019/0343168 A1 | 11/2019 | Plattner et al. |
| 2020/0170296 A1 | 6/2020 | Plunkett et al. |
| 2021/0092993 A1 | 4/2021 | Branton et al. |

FOREIGN PATENT DOCUMENTS

| | | |
|---|---|---|
| AU | 2020203674 | 6/2020 |
| CA | 2313629 | 1/2002 |
| CA | 2962906 | 4/2016 |
| CA | 3044615 | 7/2018 |
| CA | 3081522 | 8/2020 |
| CN | 105768183 | 7/2016 |
| CN | 107822195 | 3/2018 |
| CN | 110214972 | 9/2019 |
| CN | 111789298 | 10/2020 |
| CN | 107073231 | 12/2020 |
| DE | 19615422 | 11/1997 |
| DE | 19749514 | 5/1999 |
| DE | 19847968 | 4/2000 |
| DE | 69804832 | 11/2002 |
| DE | 202012011884 | 4/2013 |
| EP | 0248128 | 12/1987 |
| EP | 1145728 | 10/2001 |
| EP | 1172099 | 1/2002 |
| EP | 0892681 | 2/2002 |
| EP | 1021172 | 4/2002 |
| EP | 1027166 | 7/2002 |
| EP | 1119334 | 1/2003 |
| EP | 1027165 | 3/2003 |
| EP | 1340688 | 9/2003 |
| EP | 1297898 | 5/2004 |
| EP | 1294242 | 9/2006 |
| EP | 1944036 | 7/2008 |
| EP | 1292347 | 10/2009 |
| EP | 1677632 | 12/2009 |
| EP | 2460733 | 6/2012 |
| EP | 3093036 | 11/2016 |
| EP | 3169301 | 6/2019 |
| EP | 3542655 | 9/2019 |
| EP | 3563894 | 11/2019 |
| EP | 3610842 | 2/2020 |
| EP | 3206740 | 4/2020 |
| EP | 3729981 | 10/2020 |
| EP | 2825229 | 12/2020 |
| EP | 3788895 | 3/2021 |
| EP | 3794962 | 3/2021 |
| FR | 3032353 | 3/2017 |
| GB | 824324 | 11/1959 |
| GB | 827011 | 1/1960 |
| GB | 1013303 | 12/1961 |
| GB | 2538814 | 11/2016 |
| JP | 2010-511611 | 4/2010 |
| JP | 2012-045358 | 3/2012 |
| JP | 2013-536697 | 9/2013 |
| JP | 2016-529082 | 9/2016 |
| JP | 2017-530781 | 10/2017 |
| JP | 2018-171000 | 11/2018 |
| JP | 2020-28288 | 2/2020 |
| JP | 2015-213516 | 12/2021 |
| NL | 1027880 | 9/2006 |
| RU | 2019107930 | 10/2020 |
| TW | 201706194 | 2/2017 |
| WO | WO-94/16967 | 8/1994 |
| WO | WO-2003/095011 | 11/2003 |
| WO | WO-2008/069921 | 6/2008 |
| WO | WO-2012/033743 | 3/2012 |
| WO | WO-2013/005020 | 1/2013 |
| WO | WO-2014/083333 | 6/2014 |
| WO | WO-2014/096816 | 6/2014 |
| WO | WO-2015/009269 | 1/2015 |
| WO | WO-2015/038092 | 3/2015 |
| WO | WO-2016/059630 | 4/2016 |
| WO | WO-2016/115250 | 7/2016 |
| WO | WO-2016/124788 | 8/2016 |
| WO | WO-2017/022064 | 2/2017 |
| WO | WO-2018/083703 | 5/2018 |
| WO | WO-2018/103636 | 6/2018 |
| WO | WO-2019/105950 | 6/2019 |
| WO | WO-2019/137560 | 7/2019 |
| WO | WO-2019/166581 | 9/2019 |
| WO | WO-2019/211424 | 11/2019 |

(56) References Cited

FOREIGN PATENT DOCUMENTS

| WO | WO-2019/238749 | 12/2019 |
| WO | WO-2020/002607 | 1/2020 |
| WO | WO-2020/127261 | 6/2020 |

OTHER PUBLICATIONS

Japanese Office Action in JP App. No. 2020-097724 dated Dec. 8, 2020.
European Examination Report in EP App. No. 20177196.1, dated Mar. 23, 2021.
European Search Report in EP App. No. 20177196.1, dated Mar. 11, 2021.
Great Britain Examination Report in GB App. No. 2005160.3, dated Jun. 25, 2020.
Great Britain Examination Report in GB App. No. 2014874.8, dated Oct. 20, 2020.
Great Britain Examination Report in GB App. No. 2014874.8, dated Nov. 30, 2020.
Great Britain Examination Report in GB App. No. 2101487.3, dated Apr. 7, 2021.
Great Britain Examination Report in GB App. No. 2014874.8, dated Jun. 25, 2021.
Canadian Examination Report in Canadian App. No. 3,081,522, dated Dec. 8, 2020.
Canadian Examination Report in Canadian App. No. 3,081,522, dated Apr. 23, 2021.
International Search Report and Written Opinion in PCT/EP2021/059091, dated Jul. 14, 2021.
International Search Report and Written Opinion in PCT/EP2020/078344, dated Apr. 15, 2021.
Ramalingum, et al., "The Therapeutic Potential of Medicinal Foods", Hindawi Publishing Corporation, Advances in Pharmacological Sciences, vol. 2014, Eng. Article ID 354264, pp. 1-18.
"Nicotine: It may have a good side", Harvard Health Publishing, Harvard Medical School, Mar. 2014.

\* cited by examiner

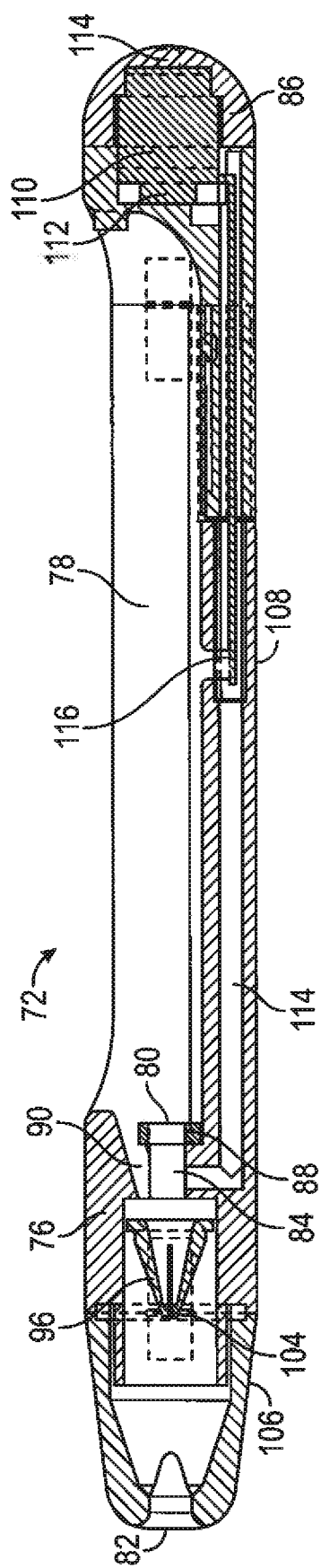
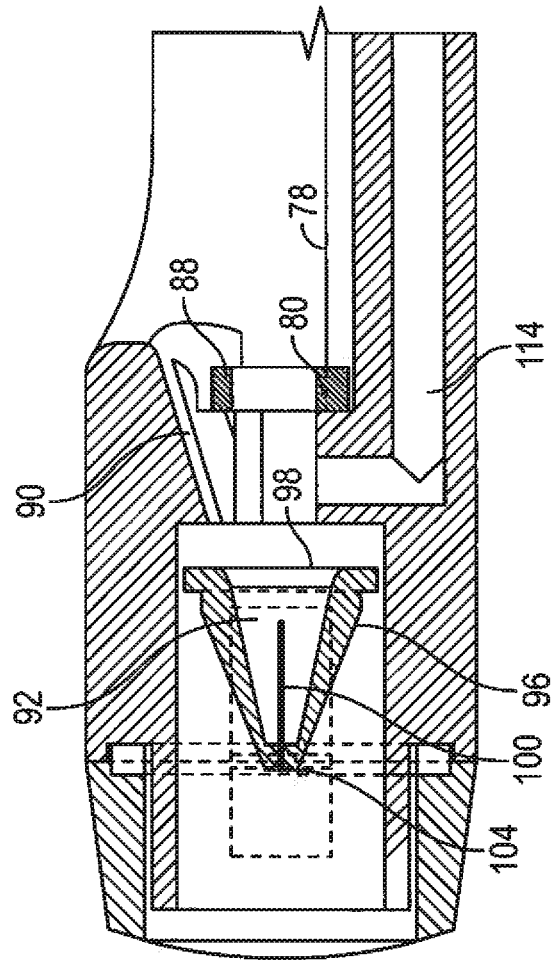
FIG. 7
FIG. 8

STABLE-FOAM DISPENSING DEVICE AND CARTRIDGE

CROSS-REFERENCE TO RELATED APPLICATIONS

This application claims priority to UK patent application No. GB 2005160.3, titled "STABLE-FOAM INHALATION DEVICE AND CARTRIDGE, filed Apr. 7, 2020, and European patent application No. EP 20177196.1, titled "STABLE-FOAM INHALATION DEVICE AND CARTRIDGE, filed May 28, 2020, the contents of which are incorporated herein by reference in their entirety.

FIELD

The present invention relates to an inhalation device and an inhalation-device cartridge. More particularly, the invention relates to a stable-foam inhalation device and cartridge. The invention further relates to a non-electrical inhalation cartridge, a method of increasing a duration of inhalation activity and an inhalation apparatus. Although described as an inhalation device, the device may also be considered to be a consumption device.

BACKGROUND

Inhalation devices typically are for users to inhale or consume substances or compounds. Such substances may have a variety of effects on the user, for example medicinal, therapeutic, stimulatory, relaxative or pleasurable effects. For example, a user may inhale medicines or tobacco components such as nicotine.

Traditional techniques for consuming or inhaling compounds such as nicotine rely on burning tobacco and either directly inhaling the smoke produced therefrom, for example as in cigarettes, or inhaling the smoke having passed through water, as in shisha or hookah. However, health concerns regarding smoke inhalation have created a need for non-smoking alternatives for inhaling compounds.

SUMMARY

Typical alternatives include vaporisers or e-cigarettes. However, these require the use of electrical energy to generate the substance which is consumed or inhaled, and therefore require regular battery charging or battery replacement. Additionally, batteries, in particular lithium batteries, can pose a fire hazard. Therefore, there are risks associated with the storage and transportation of conventional vaporisers or e-cigarettes.

Medical inhalers are known. However, such inhalers rapidly propel an aerosol into a user's respiratory system, and therefore provide a significantly different experience to smoking, which is done gradually and repeatedly by a user inhaling through a device over a prolonged duration.

It would therefore be desirable to provide a non-electrical means of producing a substance for consumption or inhalation, and which can be inhaled via a user's breath over a prolonged period. Such an alternative may also find application in pharmaceutical, health and exercise fields, as well as the food and beverage industry.

The present invention seeks to provide a solution to these problems.

According to a first aspect of the invention there is provided a stable-foam inhalation-device cartridge for a stable-foam inhalation device which dispenses a stable foam to be consumed by a user, the inhalation-device cartridge being devoid of an electrical energisation means/component and comprises: a flexible mixing chamber having a first receiving portion for slidably receiving a first foam-generation element, and a second receiving portion for slidably receiving a second foam-generation element; the flexible mixing chamber having an access opening at a first end and being closed at a second end which is opposite the said first end, the access opening being dimensioned to receive the first and second foam-generation elements therethrough; an expansion chamber which is fluidly-communicable with the access opening of the flexible mixing chamber via a partitioning element, the partitioning element having one or more mixing members for agitating a consumable foam produced by the first and second foam-generation elements as it passes from the mixing chamber to the expansion chamber; and a discharge element which is at or adjacent to one end of the expansion chamber and which has an outlet opening for enabling a user to inhale the consumable foam from the expansion chamber, the discharge element including an inlet opening and a discharge conduit which interconnects the inlet opening with the outlet opening, the discharge conduit having a longitudinal extent which locates the inlet opening at a position closer to the partitioning element than to the outlet opening.

A stable foam, as opposed to only a short-lived effervescence and/or a rapidly propelled inhalant, may allow for a user to consume or inhale a substance contained within the foam slowly, over a prolonged duration and with multiple inhalations. This can provide a satisfying and pleasurable experience for the user. The cartridge being devoid of electrical energisation means/component reduces or eliminates a requirement for electrical charging. The flexible mixing chamber provides a convenient way of activating the foam-generation elements, for example in the instance that the foam-generation elements are manually activatable. The partitioning element spaces or separates the foam-generation elements from the outlet of the cartridge, which allows for the foam to expand into the space therebetween. Such a space is here defined by the expansion chamber. The mixing members or arms of the partitioning element define apertures through which the foam moves. The movement of the foam through the apertures may generate vortices which can help to mix the foam with any unreacted foam-generation elements to improve a consistency of the foam. The discharge element with a discharge conduit allows for foam to be inhaled away from an end of the cartridge. In other words, the foam may be drawn to the outlet from a more central region of the cartridge, which may improve the consistency of foam at the outlet.

Although the mixing chamber is described as being flexible, it will be appreciated that this may not be the case. For example, in the instance of non-manual activation means being considered. Additionally or alternatively, it could be envisaged that the mixing chamber may not have an access opening as such, for example if the mixing chamber and the expansion chamber were unitarily formed.

The second end of the mixing chamber may be integrally formed with the remainder of the mixing chamber, although it will be appreciated that a separable end cap may be used.

Whilst the partitioning element is described, a partitioning element may not be strictly necessary. Alternatively, if a partitioning element is present, a mixing member may not necessarily required.

Although a discharge conduit is described for the discharge element, it will be appreciated that this may be omitted. Alternatively, if the discharge conduit is present, it would be understood that the longitudinal extent of the discharge conduit might be such that the inlet opening is closer to the outlet opening than the partitioning element.

Although the cartridge is described as being devoid of electrical energisation means, it will be appreciated that this may be included. For example, the cartridge may include an electric motor for agitating a liquid to produce foam, and a battery for energising the electric motor.

Whilst the device is described as being for a stable foam, it will be appreciated that the device may be used with other inhalants or consumables.

Preferably, the flexible mixing chamber may comprise a thermoplastic elastomer. The thermoplastic elastomer can provide a food safe, durable and sufficiently flexible material for the mixing chamber.

Advantageously, the inlet opening may be off-centre relative to the expansion chamber. In a preferable embodiment, the inlet opening may be at or adjacent to a lateral wall of the expansion chamber. Such an arrangement allows for the inlet opening to be at an in use lower position. Therefore, as the foam is consumed and a level of foam reduces in the expansion chamber, a greater total amount of foam can be accessed since the remaining foam would occupy the lower portion of the expansion chamber under gravity.

Beneficially, the partitioning element may comprise a stop, the access opening and the expansion chamber being connectable to the partitioning element either side of the stop. This allows for convenient assembly of the cartridge, since the mixing chamber and the expansion chamber can be pushed over sealing surfaces of the partitioning element until the stop is reached.

In a preferable embodiment, the stop may be a ridge which extends around the perimeter of the partitioning element.

Preferably, the partitioning element comprises an axially extending protrusion which is extendable into the flexible mixing chamber for contacting the first or second foam-generation elements. This may provide a small area of contact on the first or second foam-generation elements which may assist with discharging a liquid therefrom, for example.

Optionally, a passageway through the partitioning element may widen from the flexible mixing chamber to the expansion chamber. The widening of the passageway may encourage foam to move from the mixing chamber to the expansion chamber.

Additionally, the passageway may be widened via a step. This may permit for convenient manufacture of the widening.

Advantageously, the inhalation-device cartridge may further comprise the first and second foam-generation elements.

Beneficially, the second foam-generation element may comprise a container of liquid. A liquid allows for dissolving of the first foam-generation element.

In a preferable embodiment, the liquid may be water. Water is an ingestible liquid and can be used with a wide variety of container materials.

Additionally, the liquid may be dispensed from the container via manual pressure applied to the container. As such, the user is able to conveniently dispense the liquid from the container without a tool.

Optionally, the container may be frangible via said manual pressure. A frangible, breakable, burstable or crushable container allows for the liquid to be dispensed from an otherwise sealed container.

Preferably, the container may include a hole in an exterior wall thereof through which the passage of liquid is prevented or limited when manual pressure is not applied to the container, and through which liquid is dispensed when manual pressure is applied to the container. This has the benefit that the container is not required to be broken to dispense liquid therefrom.

Advantageously, the container may be oriented so that the hole faces the first foam-generation element. The liquid is therefore dispensed directly onto the first foam-generation element, which may reduce or eliminate a requirement to shake the cartridge to better distribute the liquid, for example.

Preferably, the container may comprise a thermoplastic elastomer. The thermoplastic elastomer can provide a food safe, durable and sufficiently flexible material.

Advantageously, the first foam generating element comprises a carbonate and an acid. This allows for effervescence by producing carbon dioxide via a chemical reaction. A chemical reaction, as opposed to, for example, releasing a pressurised container, is more convenient for manufacturing purposes.

In a preferable embodiment, the carbonate comprises sodium bicarbonate and the acid comprises citric acid. These are two ingestible or food-safe components, although other carbonates and acids may be considered.

Beneficially, the first foam generating element comprises a stabiliser. A stabiliser allows for the conversion of an otherwise short-lived effervescence into a stable foam.

Optionally, the stabiliser comprises lectin and/or xanthan gum. Other stabilisers or thickeners may also be considered.

According to a second aspect of the invention there is provided a stable-foam inhalation device for dispensing a stable foam to be consumed by a user, the inhalation device comprising the cartridge as claimed in any one of the preceding claims and a carrier, the carrier including: a carrier body; a receiving portion to receive the cartridge at or in the carrier body; a carrier inlet for fluid communication with the outlet of the discharge element when the carrier is received in or at the receiving portion; a carrier outlet to dispense a stable foam to a user; and a conduit between the carrier inlet and the carrier outlet through the carrier body.

The use of a carrier and a cartridge allows for a disposable cartridge and a reusable carrier. As such, the convenience of a pre-loaded cartridge is provided, without requiring the entire device to be disposable. The carrier can therefore be designed to be large and ergonomic as well as including additional features, without great concern for material waste since the carrier is reusable.

It will be appreciated that the discharge conduit of the cartridge may extend through at least part of the holder. In fact, the discharge conduit could extend only through the holder and may not extend through the expansion chamber.

Preferably, the stable-foam inhalation device may further comprise a one-way valve in the conduit to permit movement of foam from the carrier inlet to the carrier outlet and prevent or limit movement of fluid from the carrier outlet to the carrier inlet. As such, the user can consume or inhale foam whilst being prevented or limited from exhaling into the device and disrupting a foam-distribution therein.

Advantageously, the one-way valve may be a duck-bill valve.

Beneficially, the stable-foam inhalation device may further comprise an indication element to indicate when foam is being inhaled. This indicates to the user and/or bystanders that the device is in use.

Additionally, the indication element may comprise a light-emitting device to be lit when foam is being inhaled. Lighting may be a less intrusive signal as compared to a sound, for example. It will be appreciated that the light-emitting device does not interfere with the main functionality of the inhalation device. In other words, the user can still consume foam whether or not the light is present and operational.

Preferably, the indication element may comprise a pressure sensor. This allows for the device to detect when the user is inhaling.

Optionally, the pressure sensor may be spaced apart from the conduit, the pressure sensor being in or at a sub-conduit which is in fluid communication with the conduit. As such, the pressure sensor can be remote from the conduit outlet, which may be convenient for an electrical arrangement of the device.

Preferably, the carrier body defines the receiving portion, a part of the carrier body able to be moved relative to a remainder of the carrier body for captively holding the cartridge. A moveable part or portion of the carrier body allows for the receiving portion to be changeable in size. In other words, said part can be moved to enlarge or elongate the receiving portion so the cartridge can be positioned therein. The part can then be moved back into position so as to secure the cartridge into position.

Advantageously, the stable-foam inhalation device may further comprise a biasing element to bias said part of the carrier body towards the receiving portion. A biasing element permits for the part to be automatically moved back towards the cartridge and may secure the cartridge in place with a biasing force. This may be advantageous for users with reduced dexterity, for example users with arthritis.

Beneficially, the biasing means may be a spring.

Optionally, said part may be at or adjacent to the carrier inlet.

Preferably, the carrier body may include at least one side wall, the or each side wall including an access opening therein to provide visual or manual access to the cartridge. The access opening can, for example, permit for the cartridge to be directly engaged and moved. This may allow for the foam-generation elements to be manually manipulated through the mixing chamber walls and activated, for example. Furthermore, permitting movement of the cartridge through the access openings may assist with releasing the cartridge from the receiving portion. Alternatively or additionally, the access opening may allow for a visual inspection by the user of the production or level of foam remaining in the cartridge. The use of an access opening permits for access to the cartridge, whilst allowing for the side wall to extend further up the side of the cartridge to more securely laterally hold the cartridge in position. The access opening can also allow for leverage to be applied underneath the cartridge to assist with removal from the receiving portion.

Beneficially, the carrier body may have two side walls, each side wall having an access opening therein. Access openings in each side wall can allow for the cartridge to be gripped between fingers.

Advantageously, the carrier body and the or each access opening may be elongate, a longitudinal extent of the or each access opening being aligned with that of the carrier body. This may allow for a greater proportion of the cartridge to be visible.

Additionally, the access opening may extend towards the biasing means. This can allow for the cartridge to be conveniently moved towards the biasing element.

In a preferable embodiment, the or each access opening may be tapered.

According to a third aspect of the invention there is provided a nicotine-stable-foam inhalation device for dispensing a stable foam which comprises nicotine to be consumed by a user, the device comprising: a stable-foam inhalation-device cartridge which is devoid of electrical energisation means/component and includes a flexible mixing chamber having a first receiving portion for slidably receiving a first foam-generation element, and a second receiving portion for slidably receiving a second foam-generation element, the flexible mixing chamber having an access opening at a first end and being closed at a second end which is opposite the said first end, the access opening being dimensioned to receive the first and second foam-generation elements therethrough, an expansion chamber which is fluidly-communicable with the access opening of the flexible mixing chamber via a partitioning element, the partitioning element having one or more mixing members for agitating a consumable foam produced by the first and second foam-generation elements as it passes from the mixing chamber to the expansion chamber, a discharge element which is at or adjacent to one end of the expansion chamber and which has an outlet opening for enabling a user to inhale the consumable foam from the expansion chamber, the discharge element including an inlet opening and a discharge conduit which interconnects the inlet opening with the outlet opening, the discharge conduit having a longitudinal extent which locates the inlet opening at a position closer to the partitioning element than to the outlet opening; first and second foam-generation elements received in the first receiving portion and second receiving portion respectively, the first and/or second foam-generation element comprising nicotine; and a carrier which includes a carrier body; a receiving portion which receives the cartridge at or in the carrier body; a carrier inlet in fluid communication with the outlet of the discharge element; and a carrier outlet for dispensing the foam to the user.

According to a fourth aspect of the invention there is provided a method of consuming nicotine, the method comprising: a) assembling the nicotine-stable-foam inhalation device according to the third aspect of the invention by receiving the cartridge at the receiving portion of the carrier; b) actuating the first and/or second foam-generation elements so that the first and second foam-generation elements together produce a stable foam which comprises nicotine; and c) inhaling said stable foam from the carrier outlet.

According to a fifth aspect of the invention there is provided a *cannabis*-component-stable-foam inhalation device for dispensing a stable foam which comprises a component of *cannabis* to be consumed by a user, the device comprising: a stable-foam inhalation-device cartridge which is devoid of electrical energisation means/component and includes a flexible mixing chamber having a first receiving portion for slidably receiving a first foam-generation element, and a second receiving portion for slidably receiving a second foam-generation element, the flexible mixing chamber having an access opening at a first end and being closed at a second end which is opposite the said first end, the access opening being dimensioned to receive the first and second foam-generation elements therethrough, an expansion chamber which is fluidly-communicable with the access opening of the flexible mixing chamber via a partitioning element, the partitioning element having one or more mixing members for agitating a consumable foam produced by the first and second foam-generation elements as it passes from the mixing chamber to the expansion chamber, a discharge element which is at or adjacent to one end of the expansion chamber and which has an outlet opening for enabling a user to inhale the consumable foam from the expansion chamber, the discharge element including an inlet opening and a discharge conduit which interconnects the inlet opening with the outlet opening, the discharge conduit having a longitudinal extent which locates the inlet opening at a position closer to the partitioning element than to the outlet opening; first and second foam-generation elements received in the first receiving portion and second receiving portion respectively, the first and/or second foam-generation element comprising a *cannabis* component; and a carrier which includes a carrier body; a receiving portion which receives the cartridge at or in the carrier body; a carrier inlet in fluid communication with the outlet of the discharge element; and a carrier outlet for dispensing the foam to the user.

According to a sixth aspect of the invention there is provided a method of consuming a *cannabis* component, the method comprising: a) assembling the *cannabis*-component-stable-foam inhalation device according to a fifth aspect of the invention by receiving the cartridge at the receiving portion of the carrier; b) actuating the first and/or second foam-generation elements so that the first and second foam-generation elements together produce a stable foam which comprises a component of *cannabis*; and c) inhaling said stable foam from the carrier outlet.

According to a seventh aspect of the invention there is provided a medicine and/or dietary supplement stable-foam inhalation device for dispensing a stable foam which comprises a medicine and/or dietary supplement to be consumed by a user, the device comprising: a stable-foam inhalation-device cartridge which is devoid of electrical energisation means/component and includes a flexible mixing chamber having a first receiving portion for slidably receiving a first foam-generation element, and a second receiving portion for slidably receiving a second foam-generation element, the flexible mixing chamber having an access opening at a first end and being closed at a second end which is opposite the said first end, the access opening being dimensioned to receive the first and second foam-generation elements therethrough, an expansion chamber which is fluidly-communicable with the access opening of the flexible mixing chamber via a partitioning element, the partitioning element having one or more mixing members for agitating a consumable foam produced by the first and second foam-generation elements as it passes from the mixing chamber to the expansion chamber, a discharge element which is at or adjacent to one end of the expansion chamber and which has an outlet opening for enabling a user to inhale the consumable foam from the expansion chamber, the discharge element including an inlet opening and a discharge conduit which interconnects the inlet opening with the outlet opening, the discharge conduit having a longitudinal extent which locates the inlet opening at a position closer to the partitioning element than to the outlet opening; first and second foam-generation elements received in the first receiving portion and second receiving portion respectively, the first and/or second foam-generation element comprising a medicine and/or dietary supplement; and a carrier which includes a carrier body; a receiving portion which receives the cartridge at or in the carrier body; a carrier inlet in fluid communication with the outlet of the discharge element; and a carrier outlet for dispensing the foam to the user.

According to an eighth aspect of the invention there is provided a method of consuming a medicine and/or dietary supplement, the method comprising: a) assembling the medicine and/or dietary supplement stable-foam inhalation device according to a seventh aspect of the invention by receiving the cartridge at the receiving portion of the carrier; b) actuating the first and second foam-generation elements so that the first and second foam-generation elements together produce a stable foam which comprises a medicine and/or dietary supplement; and c) inhaling said stable foam from the carrier outlet.

According to a ninth aspect of the invention there is provided a food or drink stable-foam inhalation device for dispensing a stable foam which comprises a food or drink substance to be consumed by a user, the device comprising: a stable-foam inhalation-device cartridge which is devoid of electrical energisation means/component and includes a flexible mixing chamber having a first receiving portion for slidably receiving a first foam-generation element, and a second receiving portion for slidably receiving a second foam-generation element, the flexible mixing chamber having an access opening at a first end and being closed at a second end which is opposite the said first end, the access opening being dimensioned to receive the first and second foam-generation elements therethrough, an expansion chamber which is fluidly-communicable with the access opening of the flexible mixing chamber via a partitioning element, the partitioning element having one or more mixing members for agitating a consumable foam produced by the first and second foam-generation elements as it passes from the mixing chamber to the expansion chamber, a discharge element which is at or adjacent to one end of the expansion chamber and which has an outlet opening for enabling a user to inhale the consumable foam from the expansion chamber, the discharge element including an inlet opening and a discharge conduit which interconnects the inlet opening with the outlet opening, the discharge conduit having a longitudinal extent which locates the inlet opening at a position closer to the partitioning element than to the outlet opening; first and second foam-generation elements received in the first receiving portion and second receiving portion respectively, the first and/or second foam-generation element comprising a food or drink substance; and a carrier which includes a carrier body; a receiving portion which receives the cartridge at or in the carrier body; a carrier inlet in fluid communication with the outlet of the discharge element; and a carrier outlet for dispensing the foam to the user.

According to a tenth aspect of the invention there is provided a method of consuming a food or drink substance, the method comprising: a) assembling the food or drink stable-foam inhalation device according to a ninth aspect of the invention by receiving the cartridge at the receiving portion of the carrier; b) actuating the first and second foam-generation elements so that the first and second foam-generation elements together produce a stable foam which comprises a food or drink substance; and c) inhaling said stable foam from the carrier outlet.

According to an eleventh aspect of the invention there is provided a non-electrical inhalation cartridge for a stable-foam inhalation device which dispenses a stable foam to be inhaled by a user over a prolonged duration, the inhalation device comprising: a foam-generating-component receiving portion; stable-foam-generating components for generating the stable foam, said components being receivable at or in the component receiving portion, at least one of said components being segregated from another of said components by an openable barrier; an outlet for dispensing the stable foam to the user; a conduit which fluidly communicates the foam-generating-component receiving portion with the outlet so that when the barrier is opened the components interact to generate the stable foam which flows to the outlet via the conduit to be inhaled by the user over a prolonged duration.

According to a twelfth aspect of the invention there is provided a method of increasing a duration of inhalation activity, the method comprising the steps of: a) providing the cartridge according to the eleventh aspect of the invention; b) opening the barrier so that the foam-generating components react to generate the stable foam which flows to the outlet via the conduit; and c) inhaling the stable foam with multiple inhalations.

According to a thirteenth aspect of the invention there is provided a inhalation apparatus for dispensing an inhalant to a user, the apparatus comprising: a component receiving container comprising a flexible material; components for generating an inhalant, said components being receivable at or in the component receiving container, at least one of said components being received within a sub-container from which said at least one component is dispensable by pressure applied to the sub-container via flexion of the component receiving container; an outlet for dispensing the inhalant to the user; a conduit which fluidly communicates the component receiving container with the outlet so that when said at least one component is dispensed from the sub-container the components interact to generate the inhalant which flows to the outlet via the conduit to be inhaled by the user.

According to a fourteenth aspect of the invention there is provided a stable-foam inhalation device to dispense a stable foam which comprises at least one of the following to be consumed by a user: nicotine, a component of *cannabis*, a medicine and/or dietary supplement, and a food or drink, the device comprising: a stable-foam inhalation-device cartridge which is devoid of an electrical energisation component and includes a flexible mixing chamber having a first receiving portion to slidably receive a first foam-generation element, and a second receiving portion to slidably receive a second foam-generation element, the flexible mixing chamber having an access opening at a first end and being closed at a second end which is opposite the said first end, the access opening being dimensioned to receive the first and second foam-generation elements therethrough, an expansion chamber which is fluidly-communicable with the access opening of the flexible mixing chamber via a partitioning element, the partitioning element having one or more mixing members to agitate a consumable foam produced by the first and second foam-generation elements as it passes from the mixing chamber to the expansion chamber, a discharge element which is at or adjacent to one end of the expansion chamber and which has an outlet opening to enable a user to inhale the consumable foam from the expansion chamber, the discharge element including an inlet opening and a discharge conduit which interconnects the inlet opening with the outlet opening, the discharge conduit having a longitudinal extent which locates the inlet opening at a position closer to the partitioning element than to the outlet opening; first and second foam-generation elements received in the first receiving portion and second receiving portion respectively, the first and/or second foam-generation element comprising at least one of the following: the nicotine, the component of *cannabis*, the medicine and/or dietary supplement, and the food or drink; and a carrier which includes a carrier body; a receiving portion which receives the cartridge at or in the carrier body; a carrier inlet in fluid communication with the outlet of the discharge element; and a carrier outlet to dispense the foam to the user.

According to a fifteenth aspect of the invention there is provided a method of consuming at least one of the following: nicotine, a *cannabis* component, a medicine and/or dietary supplement, and a food or drink substance, the method comprising: a) assembling the stable-foam inhalation device according to the fourteenth aspect of the invention by receiving the cartridge at the receiving portion of the carrier; b) actuating the first and/or second foam-generation elements so that the first and second foam-generation elements together produce a stable foam which comprises at least one of the following: the nicotine; the *cannabis* component, the medicine and/or dietary supplement, and the food or drink substance; and c) inhaling said stable foam from the carrier outlet.

BRIEF DESCRIPTION OF THE DRAWINGS

The invention will now be more particularly described, by way of example only, with reference to the accompanying drawings, in which:

FIG. 7 shows a side cut away view of the stable-foam inhalation device of FIG. 6 without the stable-foam inhalation-device cartridge;

FIG. 8 shows an enlarged view of an inlet of the stable-foam inhalation device of FIG. 6 without the stable-foam inhalation-device cartridge;

DETAILED DESCRIPTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Figure 1:
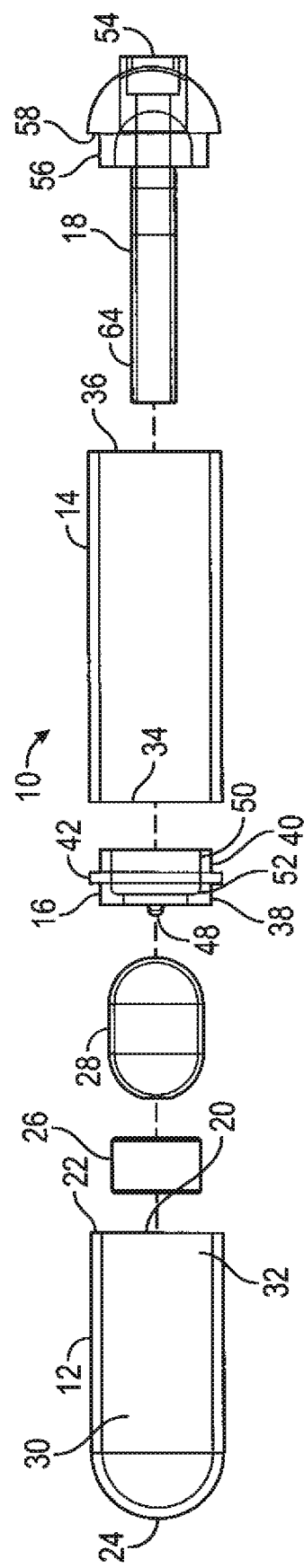
FIG. 1 shows a top view of a first embodiment of a stable-foam inhalation-device cartridge according to first and eleventh aspects of the invention.
Figure 2:
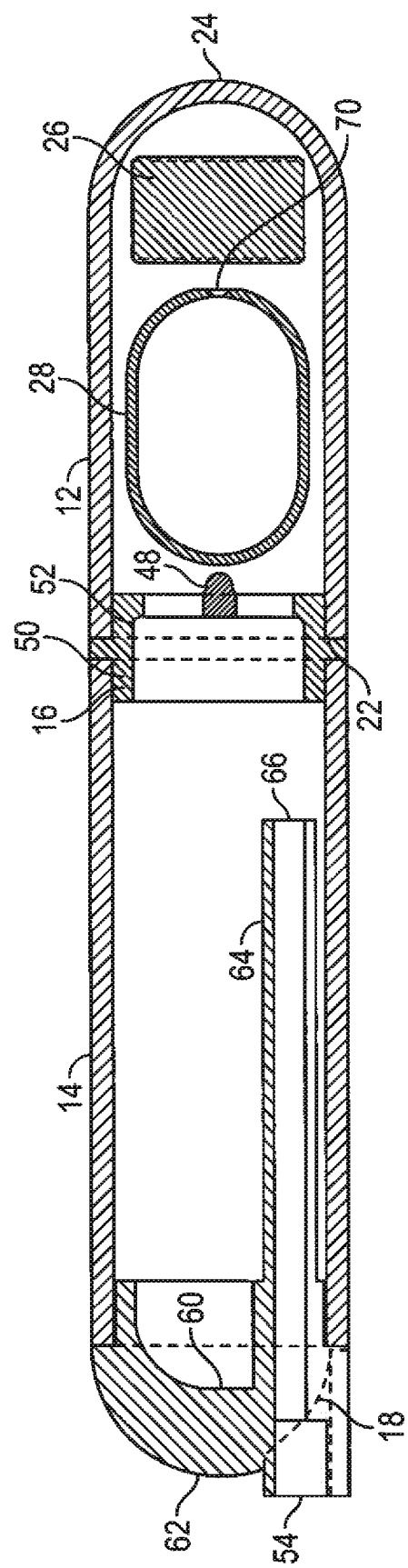
FIG. 2 shows a side view of the stable-foam inhalation-device cartridge of FIG. 1.
Figure 3:
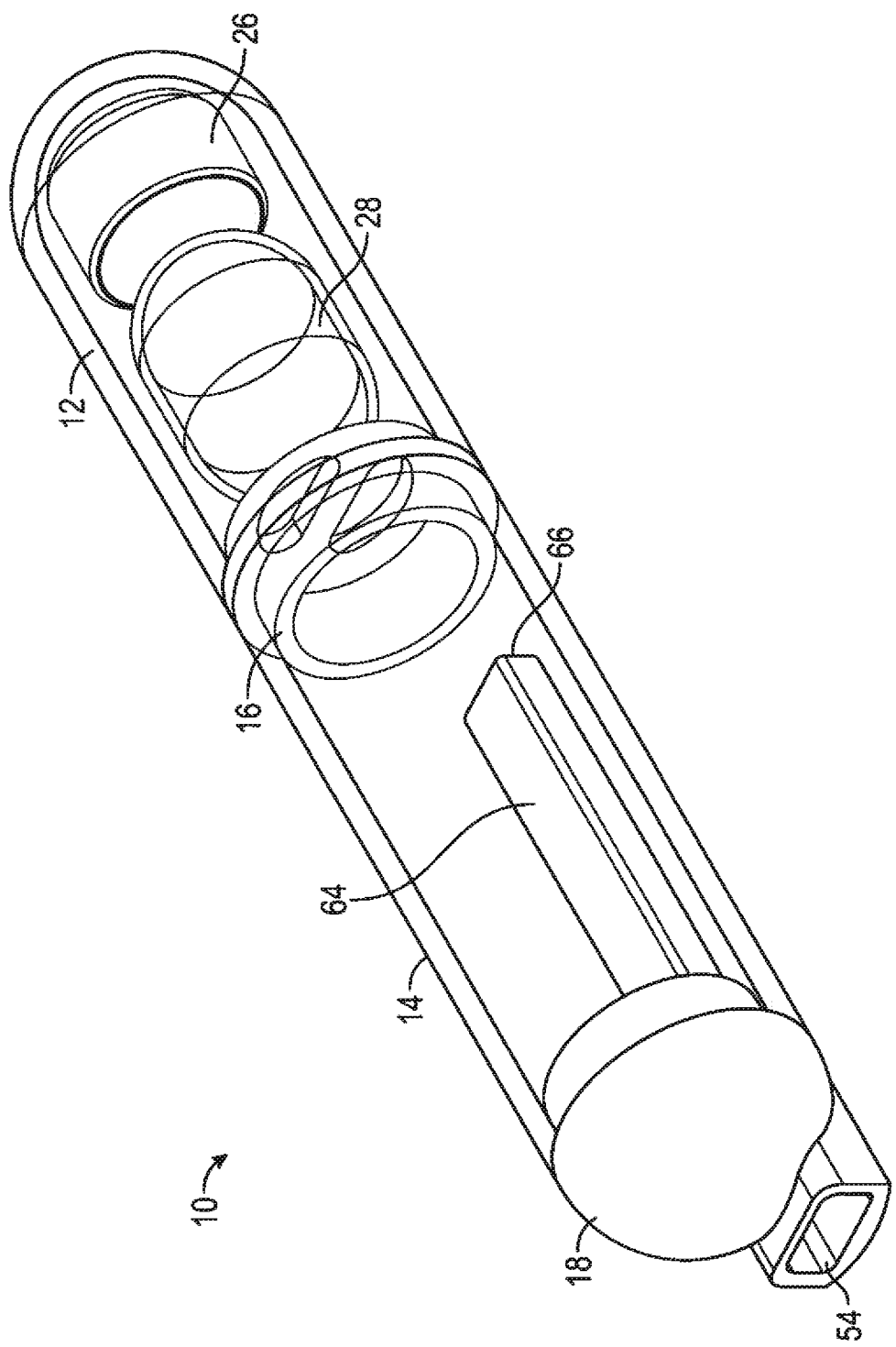
FIG. 3 shows a perspective view of the stable-foam inhalation-device cartridge of FIG. 1.

Referring firstly to FIGS. 1 to 3 there is shown a first embodiment of a stable-foam inhalation-device cartridge 10. The inhalation-device cartridge 10 comprises a flexible mixing chamber 12, an expansion chamber 14, a partitioning element 16, and a discharge element 18.

The flexible mixing chamber 12 has an access opening 20 at a first end 22 and is closed at a second end 24 which is opposite the first end 22. The access opening 20 is dimensioned to receive first and second foam-generation elements 26, 28 therethrough. The access opening 20 is circular or substantially circular in shape, although it will be appreciated that other shapes may be considered such as square or triangular. Similarly, the flexible mixing chamber 12 has a circular cross-section, although other shapes may be considered. Preferably, the second end 24 is curved such that an end portion associated with the second end 24 may be considered to be semi-spherical. However, this may not be necessary, and the second end 24 could be planar or flat.

The flexible mixing chamber 12 has a first receiving portion 30 for slidably receiving the first foam-generation element 26, and a second receiving portion 32 for slidably receiving the second foam-generation element 28. The first receiving portion 30 is distal to the access opening 20 as compared to the second receiving portion 32 and is here at or adjacent to the second end 24. The second receiving portion 32 is at or adjacent to the access opening 20. The flexible mixing chamber 12 is preferably sized so that the first receiving portion 30 and the second receiving portion 32 together are defined across a majority of the length of the flexible mixing chamber 12, and more preferable are defined across substantially the entire length of the flexible mixing chamber 12.

The flexible mixing chamber 12 preferably comprises a thermoplastic elastomer which provides the desired flexibility of the mixing chamber 12. However, it will be appreciated that other flexible materials may be considered such as silicone, other elastomeric materials, for example rubber, or other flexible plastics. The flexibility of the mixing chamber 12 allows for compressive manual actuation or activation of the first and/or second foam-generation elements. However, in the instance of other actuation or activation methods, the mixing chamber 12 may not necessarily be flexible. The flexible mixing chamber 12 may preferably be transparent or translucent.

The expansion chamber 14 is preferably cylindrical or substantially cylindrical and may be considered to be a tube. However, other shapes may be considered. For example, the expansion tube may have a cross-sectional shape of that of a flattened circle. In other words, the expansion tube may have an elliptical cross-section. Any other shape may be considered, for example rectangular or triangular. This may similarly apply to the mixing chamber 12, partitioning element 16 and discharge element 18. The expansion chamber 14 preferably has a mixing-chamber proximal opening 34 and a discharge-element proximal opening 36. Here each opening is identical, although it will be appreciated that this may not necessarily be the case. The expansion chamber 14 is also formed from a flexible material, such as a thermoplastic elastomer, although it will be appreciated that this may not be necessary. The expansion chamber 14 may preferably be transparent or translucent.

The mixing-chamber proximal opening 34 of the expansion chamber 14 is fluidly communicable with the access opening 20 of the flexible mixing chamber 12 via the partitioning element 16. The partitioning element 16 preferably sealingly connects the expansion chamber 14 with the flexible mixing chamber 12. In other words, the partitioning element 16 connects and seals the expansion chamber 14 and the mixing chamber 12 together to prevent leakage of foam.

To achieve the sealing connection, the partitioning element 16 has mixing-chamber sealing surface 38 and an expansion-chamber sealing surface 40. Preferably each sealing surface 38, 40 is annular or substantially annular. Diameters of the mixing-chamber sealing surface 38 and an expansion-chamber sealing surface 40 are similar or identical to the diameters of the access opening 20 and the mixing-chamber proximal opening 34 of the expansion chamber 14 respectively. This is such that the sealing surfaces 38, 40 form an interference fit with the relevant opening and/or end portion of the expansion chamber 14 or mixing chamber 12. This prevents or limits leakage of foam or other components from either chamber. The sealing surfaces 38, 40 are receivable within the respective chamber to abut the inside wall thereof. The access opening 20 and the mixing-chamber proximal opening 34 preferably have similar or identical diameters and as such it will be appreciated that either sealing surface could feasibly be used for either opening. However, this may not be the case and the diameters of the access opening 20 and the opening of the expansion chamber 14 may be different.

The partitioning element 16 preferably comprises an exterior stop 42, the mixing chamber 12 and the expansion chamber 14 being connectable to the partitioning element 16 either side of the stop 42. The stop 42 is here a ridge which extends annularly around a perimeter of the partitioning element 16 and separates the two sealing surfaces 38, 40 from each other.

Figure 4:
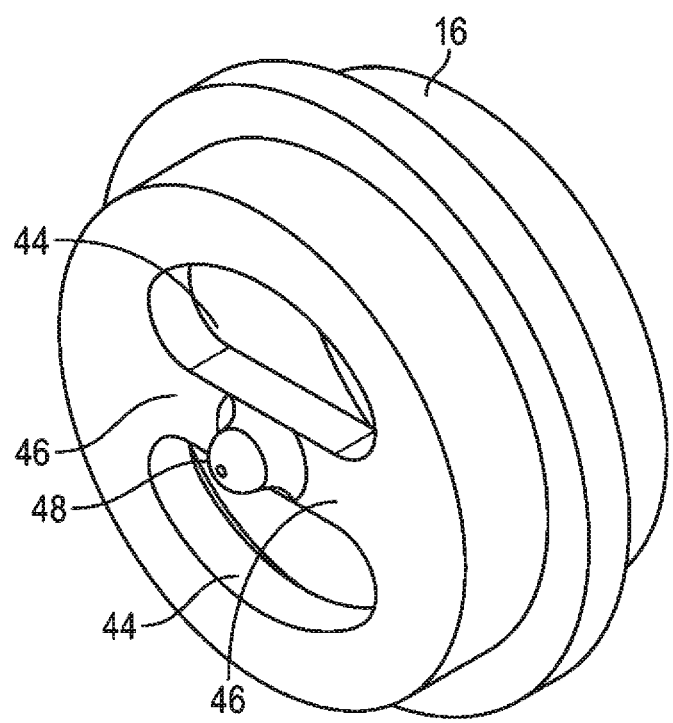
FIG. 4 shows a perspective view of a partitioning element of the stable-foam inhalation-device cartridge of FIG. 1.
Figure 5:
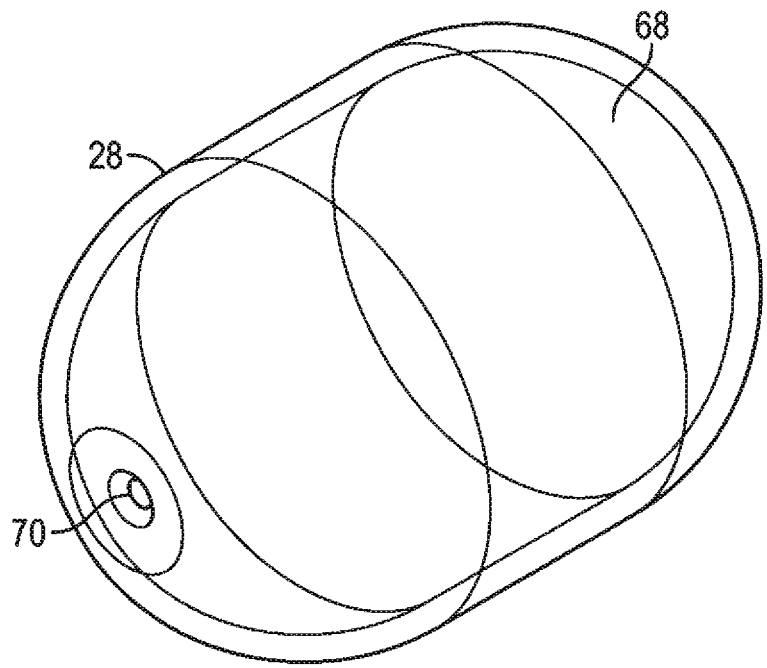
FIG. 5 shows a perspective view of a second foam-generation element of the stable-foam inhalation-device cartridge of FIG. 1.

Referring now to FIG. 4, the partitioning element 16 further comprises at least one hole 44 or through-bore for fluidly communicating the expansion chamber 14 with the access opening 20. Preferably, there are two separate holes 44, the holes 44 separated by at least one, and here two, mixing members 46. The mixing members 46 may be considered to be arms. Additionally, the mixing members 46 may prevent or limit the movement of the foam-generation elements in their initial form from the mixing chamber 12 to the expansion chamber 14. The holes 44 are preferably curved and/or the openings of the holes 44 are elongate such that the holes 44 may be considered to be slots.

The partitioning element 16 may additionally include a protrusion 48 which may extend axially into the mixing chamber 12. One protrusion 48 is shown, although it will be anticipated that multiple protrusions 48 may be considered. Additionally, the protrusion 48 is shown to be central on the partitioning element 16, although it will be appreciated that it may be off-centre. The protrusion is preferably tapered or pointed. In some instances, a side wall of the mixing chamber could also include a protrusion.

Referring again to FIGS. 1 and 2 a passageway 50, at least in part defined by the holes 44, through the partitioning element 16 widens from the mixing-chamber sealing surface 38 to the expansion-chamber sealing surface 40. This widening of the passageway 50 is preferably abrupt, for example being formed by a step 52.

The discharge element 18 is at or adjacent to one end of the expansion chamber 14 and has an outlet opening 54 for dispensing or discharging foam therefrom. The discharge element 18 here closes the discharge-element proximal opening 36 at said end of the expansion chamber 14. As such, the discharge element 18 includes a sealing surface 56 which connects with and seals the expansion chamber 14 in the same or a similar way as the sealing surfaces of the partitioning element 16. The sealing surface 56 of the discharge element 18 is therefore annular, has a diameter which is similar or identical to that of the proximal opening of the expansion chamber 14 and is receivable therein. The discharge element 18 further includes a stop 58 to prevent over-insertion of the discharge element 18 into the expansion chamber 14.

An interior surface 60 of the discharge element 18 is concave or substantially concave which may assist with redirecting foam. An exterior surface 62 of the discharge element 18 is convex.

The outlet opening 54 preferably protrudes and/or is separated from the exterior surface of a body of the discharge element 18. The outlet opening 54 is off-centre relative to the remainder of the discharge element 18, being at or adjacent to an in use lower portion of the discharge element 18.

The discharge element 18 further includes a discharge conduit 64 and an inlet opening 66, the discharge conduit 64 interconnects the inlet opening 66 and the outlet opening 54 so that they are in fluid communication. The discharge conduit 64 has a longitudinal extent which locates the inlet opening 66 at a position closer to the partitioning element 16 than to the outlet opening 54. Additionally, the inlet opening 66 is located off-centre relative to the remainder of the discharge element 18 and/or the expansion chamber 14. In use, the inlet opening 66 is preferably at or adjacent to a lower interior surface of the expansion chamber 14.

The flexible mixing chamber 12 includes first and second foam-generation elements 26, 28. These are positioned inside the mixing chamber 12 in the corresponding receiving portions 30, 32. With the foam-generation elements 26, 28 received therein, the partitioning element 16 is connected to the mixing chamber 12, the expansion chamber 14 is connected to the partitioning element 16 and the discharge element 18 is connected to the expansion chamber 14. These parts may be adhered together to prevent disassembly or separation. Additionally, it will be appreciated that two or more of the parts may be unitarily formed together.

When the substances which comprise the first and second foam-generation elements 26, 28 are reacted or interacted together they produce a stable foam. This is preferably achieved by effervescence which is stabilised and/or thickened into a foam.

For example, the first foam-generation element 26 comprises a carbonate, for example sodium bicarbonate, and an acid, for example citric acid. Although sodium bicarbonate and citric acid are preferred, it will be appreciated that any other ingestible or food safe carbonate, for example calcium carbonate, or acid, for example tartaric acid, may be considered. The carbonate and the acid are here in solid form, for example being powdered and compressed into the first foam-generating element. The first foam-generating element may therefore be considered to be a tablet or pill, although it will be appreciated that it may be uncompressed and simply be a powder. In the solid form, the carbonate and acid do not react. The first foam-generation element 26 further comprises a stabiliser and/or thickener. Here stabilisers and/or thickeners such as lecithin and xanthan gum are used; however, any thickening or stabilising agent may be considered.

The cross-sections of each of the first and second foam-generation elements 26, 28 are preferably circular so as to correspond to the cross-section of the flexible mixing chamber.

Figure 6:
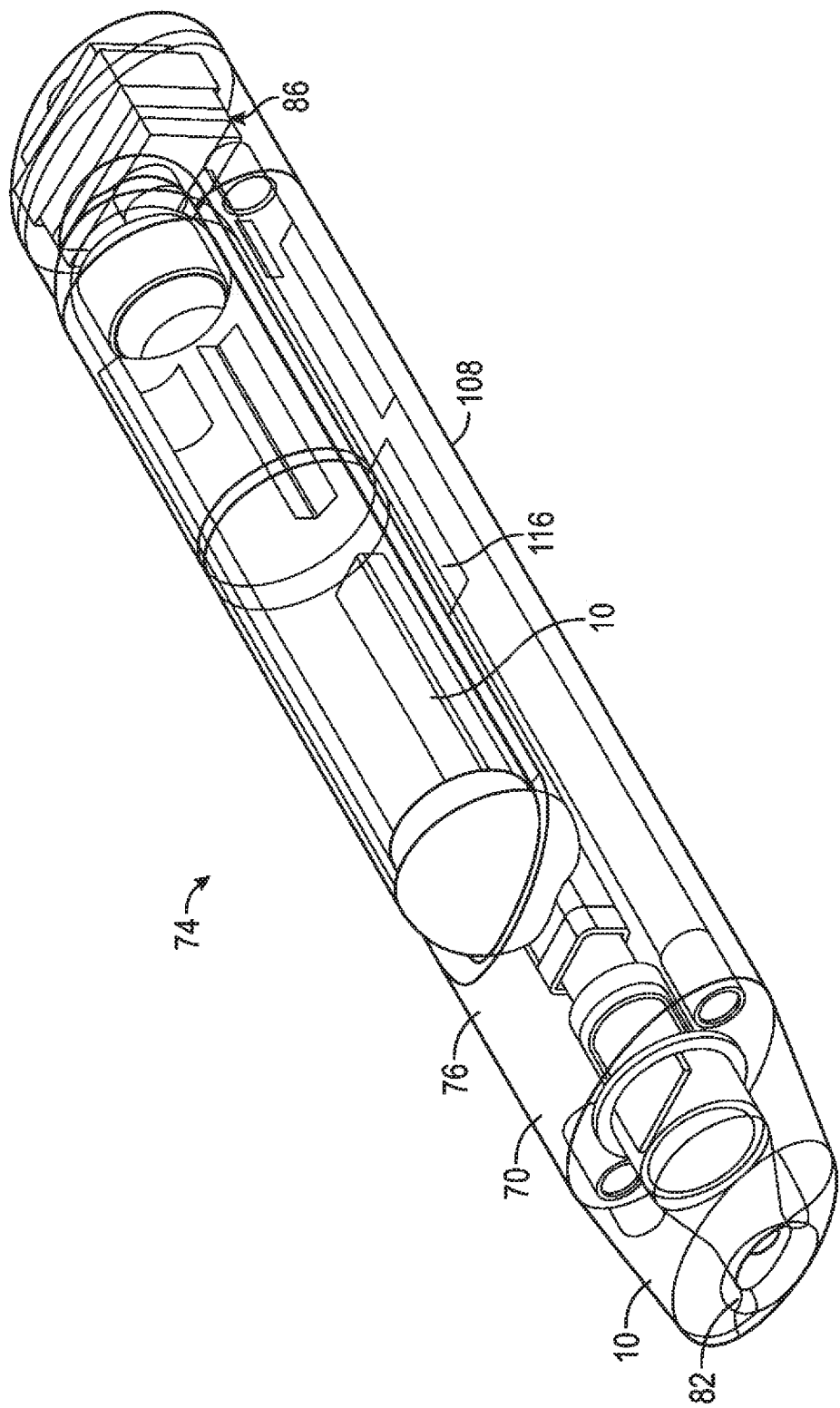
FIG. 6 shows a perspective view of a stable-foam inhalation device according to a second aspect of the invention, with the stable-foam inhalation-device cartridge of FIG. 1 therein.

Referring in particular to FIG. 6, the second foam-generation element 28 preferably comprises a container 68 of liquid. For example, here the second container 68 comprises a container 68 of water, although other liquids may be considered. The water may include a colourant which may assist with visual identification thereof. The container 68 is hollow, sealed and preferably has curvate ends, for example here a longitudinal cross-section of the container 68 has a stadium shape. However, other shapes may be considered, such as a ball shape. In fact, a container 68 as such may not be used and the liquid and the first foam-generation element 26 may be separated or segregated by a planar seal.

The container 68 is preferably flexible, and may be formed from a thermoplastic elastomer although other flexible materials may be considered as before. In the instance of a flexible container, the container 68 preferably includes a hole 70 therein, the hole 70 allowing for the liquid to be ejected therefrom when the container 68 is squeezed. The hole 70 is preferably small, such that when pressure is not applied the surface tension of the liquid maintains the liquid in the container 68. For example, the diameter of the hole 70 may be between 0 mm and 1 mm, and may more preferably be substantially 0.5 mm, for example being 0.45 mm. The flexible container 68 with a hole 70 therein is preferably referred to as a squeeze ball. The hole 70 is ideally in an end of the container and is oriented so as to face the first foam-generation element 26.

However, the container 68 may not be flexible and may be rigid. In the instance of a rigid or inflexible container 68, at least part of the container 68 is preferably frangible via manual pressure applied thereto and may be burstable or crushable. Breaking of at least part of the container 68 may release fluid therefrom. In the instance that the container 68 is rigid, the hole 70 therein may still be present, although it will be appreciated that this may not be necessary.

Although the liquid preferably comprises, consists or consists essentially of water, it will be appreciated that the liquid may instead be an acidic solution or a carbonate solution, and the first foam-generation element 26 may lack the acid or the carbonate.

The first and/or second foam-generation elements 26, 28 may include additional components which a user may wish to consume or inhale. In particular, the first and/or second foam-generation elements 26, 28 could include flavourings to improve a user-experience. Further additional components are discussed below.

For example, the first and/or second foam-generation elements 26, 28 may include pharmaceuticals, medicines and/or dietary supplements. This may include vitamins, exercise supplements such as pre-workout compositions, branched-chain amino acids, creatine, other supplements usually taken during a workout for endurance, over-the-counter style medicines such as cough or pain remedies and/or erectile dysfunction medicine such as sildenafil. Compounds which are taken in small doses to be ingested as and when needed are of particular relevance.

The first and/or second foam-generation elements 26, 28 may include a food or beverage substance, or a compound thereof. This may include flavourings or components of soft drinks, for example electrolyte type sports drinks or iced tea, both of which can conventionally be found in powdered form. Alcoholic drinks may be considered, and in this case alcohol could be used as the liquid in the container 68. Flavourings or components of confectionary or desserts may also be considered, which may allow a user to experience a confectionary or dessert without consuming the number of calories typically associated therewith. The first and/or second foam-generation elements 26, 28 may include caffeine, for example a total caffeine content of the first and/or second foam-generation elements 26, 28 being substantially equivalent to a conventional espresso shot.

The first and/or second foam-generation elements 26, 28 may include nicotine and therefore may provide an alternative to smoking. The first and/or second foam-generation elements 26, 28 may also include other components of tobacco or tobacco itself.

The first and/or second foam-generation elements 26, 28 could include *cannabis* or components of *cannabis*, for example including tetrahydrocannabinol (THC) and/or cannabidiol (CBD) to provide psychoactive and/or medicinal effects as desired. Although *cannabis* is described in this specification, in view of the different legal and moral statuses of *cannabis* worldwide, it will be appreciated that reference to *cannabis* and/or components thereof may be deleted from the specification if necessary.

As shown in FIGS. 6 and 7, the cartridge 10 is received in a first embodiment carrier 72 or holder to form the first embodiment of an inhalation device 74. The carrier 72 comprises a carrier body 76, a cartridge receiving portion 78 for receiving the cartridge 10 at or in the carrier body 76, a carrier foam inlet 80, a carrier outlet 82 and a passageway 84 or conduit between the carrier foam inlet 80 and the carrier outlet 82 through the carrier body 76.

The cartridge receiving portion 78 is here a hole 44 or recess in the carrier body 76 and is sized to captively hold the cartridge 10. A rear part 86 of the carrier body 76 is removably attachable to the remainder of the carrier body 76 so as to allow insertion of the cartridge 10.

The outlet opening 54 of the cartridge 10 is fluidly communicable with the carrier foam inlet 80 of the carrier 72, and may be insertable therein. The carrier foam inlet 80 includes a seal 88 for sealing the outlet opening 54 of the cartridge 10 thereto. The seal 88 is preferably an O-ring, and may be elastomeric.

At or adjacent to the carrier foam inlet 80 is a carrier air inlet 90. The air inlet 90 allows for the addition of air to or the entrainment of air with the foam. The air inlet 90 is preferably a channel or conduit through the carrier body 76 to the exterior of the device. Alternatively, the air inlet 90 might feasibly be or communicable with a void in the carrier body 76.

A venturi tube 92 is preferably fluidly communicable with the carrier foam inlet 80 and is preferably also fluidly communicable with the carrier air inlet 90. The venturi tube 92 has a rear opening which is communicable with both inlets 80, 92. A passageway through the tube 92 may taper to increase a speed of flow of fluid therethrough, although it will be appreciated that this may not be strictly necessary. A head portion of the venturi tube 92 has a tapered and preferably frusto-conical shape. The venturi tube 92 may help to mix the foam and the air together.

The carrier 72 further includes a one-way valve 96 between the carrier foam inlet 80 and a carrier outlet 82. The one-way valve 96 is arranged to prevent a user from exhaling into the cartridge 10 or device and disrupting a foam distribution therein. The one-way valve 96 is preferably a duck-bill valve 96. The duck-bill valve 96 comprises a flexible material and is conical or substantially conical in shape, having an opening 98 at a base. The valve 96 includes a cut 100 part of the way along a body of the valve 96 from the tip or forward part of valve 96. The cut 100 allows for fluid to flow from the base and out of the tip. This is since the portions of the body demarcated by the cut 100 separate from each other to create a forward opening in the valve 96 when under outward-pressure from the interior of the of the body of the valve. When a tip portion 104 is under inward pressure from the exterior of the body of the valve, the portions of the body demarcated by the cut 100 remain in contact to prevent fluid flow therethrough.

The tapered end of the venturi tube 92 is preferably received through the opening 98 in the base of the one-way valve 96.

A front part 106 of the carrier body 76 is preferably removable from the remainder of the body 76 and/or a central part 108 of the carrier body 76, for example to assist with cleaning. The front part 106 could include the one-way valve 96 and/or the venturi tube 92, although this is not the case as shown. The front part 106 and/or the central part 108 of the carrier body 76 may include magnetic elements to allow for convenient detachable attachment therebetween. The carrier 72 may also include a sealing element between the front part 106 and the central part 108.

Figure 9:
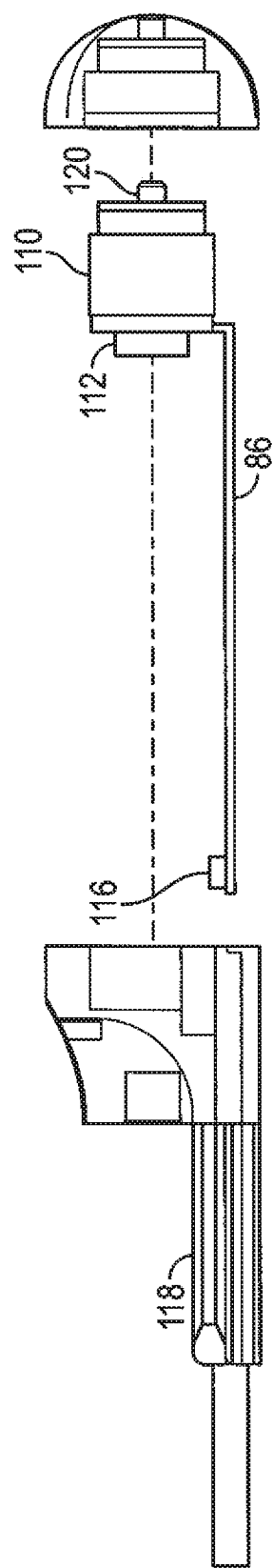
FIG. 9 shows an exploded view of a rear part of the stable-foam inhalation device of FIG. 6.
Figure 10:
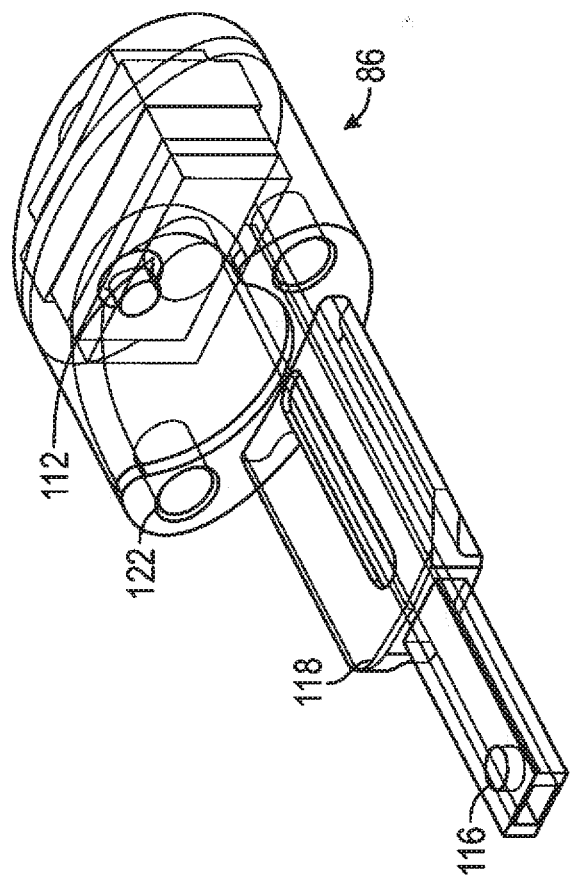
FIG. 10 shows a perspective view of the assembled rear part of FIG. 9.

Referring to FIGS. 8 to 10 in particular, the inhalation device 74 may also include an indication or signalling means or element 110 for indicating or signalling when a user is inhaling from the inhalation device 74. The indication element 110 may include a pressure or flow sensor 112 for detecting when negative pressure is applied thereto. As shown in FIG. 8, a conduit 114, sub conduit or channel extends from the passageway 84 between the carrier foam inlet 80 and the carrier outlet 82 to the flow sensor 112. The flow sensor 112 is preferably positioned in or at the rear part 86 of the carrier 72. However, in some instances the pressure sensor 112 may be directly at or in the passageway.

The indication element 110 further includes a light-emitting device 116, such as a light emitting diode, which is configured to light when a negative pressure is sensed by the pressure sensor 112. The light-emitting device 116 is preferably positioned within the carrier body 76 and at or adjacent to the cartridge 10. For example, being at or adjacent to a central region of the cartridge receiving portion 78 of the carrier 72. To accommodate the light-emitting device 116 in this position, the rear carrier part 86 may include a projecting portion 118 which projects from a body portion of the rear carrier part 86 and supports the light-emitting device 116 and wiring or an electrical track. The central part 108 of the carrier 72 may include a hole for receiving the projecting portion 118.

The light-emitting device 116 is electrically, electronically or communicatively connected with the pressure sensor 112. The indication element 110 may include a controller configured to determine when the flow sensor 112 measures a negative pressure and then instruct the light-emitting device 116 to illuminate.

The indication element 110 preferably includes a battery to power the light-emitting device 116, pressure sensor 112, and controller if present. The battery is preferably a rechargeable battery and the carrier 72 includes an electrical terminal 120 for recharging the battery.

It will be appreciated that the indication element 110 may not be essential for the device to dispense foam and so may not be included. As such, for the purpose of dispensing foam, the device is devoid of electrical components and/or is non-electrically-energisable.

Referring in particular to FIG. 10, the rear carrier part 86 preferably includes part of the cartridge receiving portion 78. The rear carrier part 86 may include at least one magnetic element 122 for releasably coupling with magnetic elements on the central part 108 of the carrier body 76. This may allow for the rear part 86 to be conveniently detachably attachable to the central part 108.

In use, the cartridge receiving portion 78 is opened by removing the rear carrier part 86. The cartridge 10 is positioned in the cartridge receiving portion 78 and the cartridge receiving portion 78 is closed by reattaching the rear carrier part 86. When in the cartridge receiving portion 78, the outlet opening 54 of the discharge element 18 is inserted or connected with the carrier foam inlet 80 of the carrier 72.

A user may then apply pressure to the flexible mixing chamber 12 over the second foam-generation element 28. The flexible mixing chamber 12 thus deforms and causes pressure to be applied to the second foam generation element 28 which causes liquid to be ejected or dispensed from the container 68 via the hole 44. The protrusion 48 of the partitioning element 16 may assist with ejecting liquid from the container 68, since it may limit the container 68 from deforming in a direction towards the partitioning element 16. A point pressure applied by the protrusion 48 may cause additional pressure on the container 68 to encourage dispensation of the liquid.

The liquid causes the components or chemicals in the first foam-generation element 26 to dissolve. The carbonate and the acid are thus able to react to produce carbon dioxide and thereby effervesce. This effervescence, which would otherwise be short-lived, is stabilised into a stable foam by the stabiliser. The foam is thickened by the thickener.

Although a stabiliser for stabilising carbon dioxide bubbles is preferred for forming a stable foam, it will be appreciated that other methods may be utilised for forming a stable foam. For example, nitrogen gas may be utilised to generate a small bubble size which may be more stable than a conventional carbon dioxide bubble. Although a chemical reaction is described as producing the effervescence and foam, it will be appreciated that other methods of effervescence or foam generation may be considered. For example, a pressurised container 68 of gas may be released, or a liquid may be agitated to produce a foam.

As the foam is generated it may move out of the mixing chamber 12 and into the expansion chamber 14 where expansion of the foam is accommodated. The mixing arms of the partitioning element 16 mix the foam as it passes through the partitioning element 16. This mixing is accomplished by the mixing arms generating a vortex in the foam as the foam passes through the apertures defined by the mixing arms. The mixing assists with dissolving the first foam-generation element 26 and therefore can prevent or limit powder from being inhaled.

The user may then inhale from or at the carrier outlet 82. The negative pressure or suction applied by the inhalation causes the duck-bill valve 96 to open and foam is drawn from the expansion chamber 14, along the discharge conduit 64 and into the carrier foam inlet 80. The foam is mixed with air which is drawn through the carrier air inlet 90. The foam and air mix passes through the venturi tube 92, through the open duck-bill valve 96 and into the user's mouth via the carrier outlet 82.

The user only inhales part of the foam with a single inhalation. Since the foam is stable, the foam may be inhaled multiple times over a prolonged duration. For example, the foam is stable or present for between 15 and 30 minutes and allows for a plurality of inhalations of foam, for example substantially 50 inhalations.

When the user inhales from the carrier outlet 82, this causes a negative pressure to act on the pressure sensor 112 which triggers the illumination of the light-emitting device 116. This provides an indication to the user and/or others that the device is being used.

Once the foam has been utilised or dispensed, the user may remove the cartridge 10 by detaching the rear carrier part 86. A new cartridge 10 may then be inserted into the cartridge receiving portion 78 as required.

Figures 11, 12:
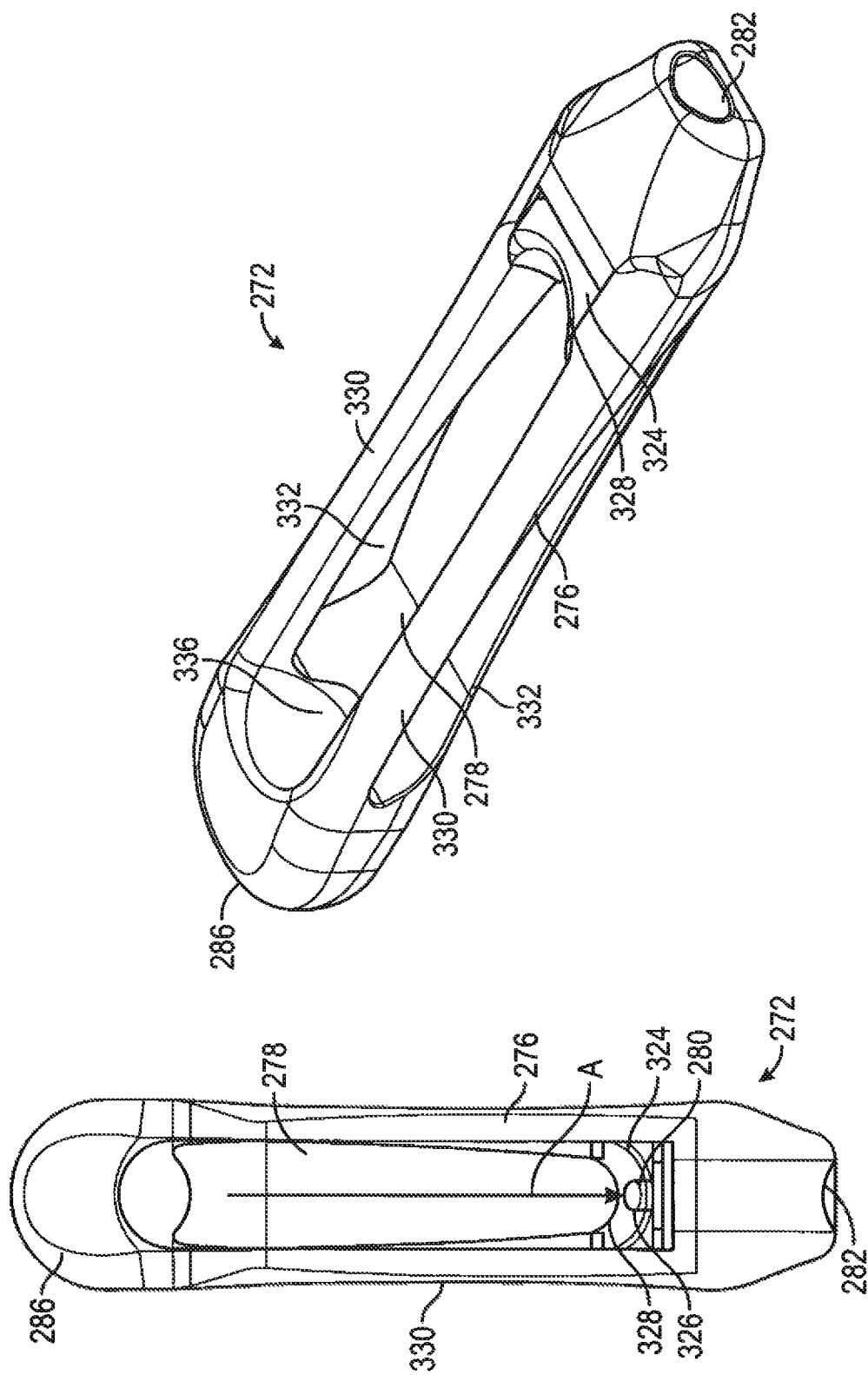
FIG. 11 shows a top view of a carrier of a second embodiment of a stable-foam inhalation device in accordance with first and eleventh aspects of the invention, a block arrow showing a direction of insertion of a cartridge.
FIG. 12 shows a perspective view of the carrier of FIG. 11.
Figure 13:
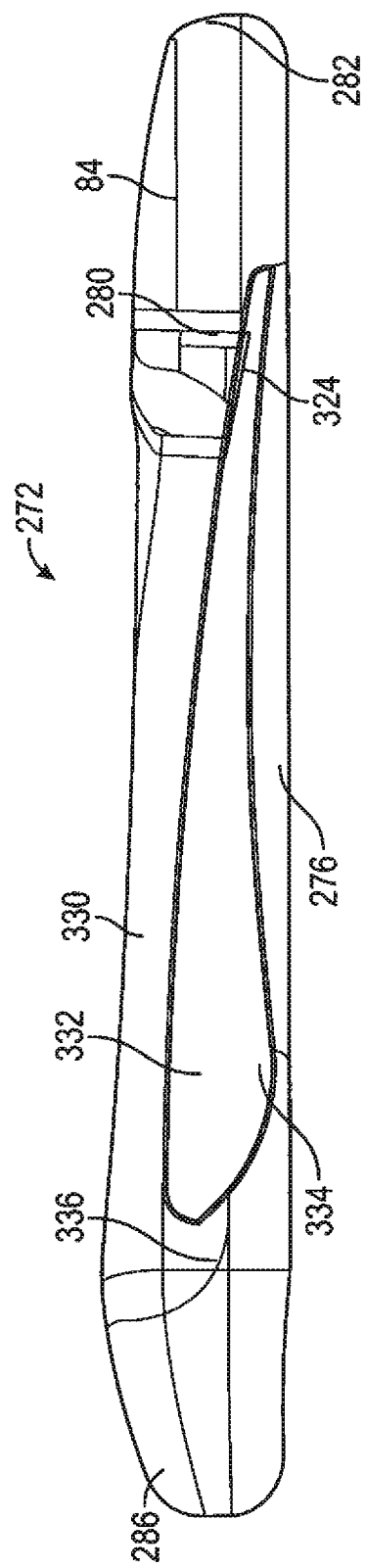
FIG. 13 shows a side view of the carrier of FIG. 11.

Referring now to FIGS. 11 to 13, there is shown a second embodiment of a carrier 272 of a stable foam inhalation device. A cartridge, such as that previously described, is receivable in the carrier 272 to form the inhalation device. Similar or identical reference numerals are used as for the first embodiment, with 200 added. The second embodiment of the carrier 272 is preferably similar to the first embodiment 72 and has at least some similar or identical features.

The carrier body 276 of the second embodiment of the carrier 272 includes a moveable part 324 or portion at or adjacent to the cartridge receiving portion 278, and at or adjacent to the carrier foam inlet 280. An edge of the moveable part 324 may define part of the receiving portion 278. The moveable part 324 is preferably moveable so as to be received further towards the carrier outlet 282, and therefore away from a centre of the receiving portion 278. This would enlarge or elongate the receiving portion 278. The carrier body 276 may include grooves and/or a recess to accommodate the movement of the moveable part 324 towards the carrier outlet 282. However, it will be appreciated that the moveable part may be at another location at or adjacent to the receiving portion, for example being adjacent to a rear end of the carrier body. In this case, the moveable part would be moveable towards the rear end, and so away from the centre of the receiving portion.

The moveable part 324 is preferably biased towards the receiving portion 278 via a biasing means. This may be achieved via the use of a spring. For example, a coil spring may be mounted between the moveable part 324 and a remainder of the carrier body 276 which forces the moveable part 324 towards the receiving portion 278. The carrier body 276 may include a stop for the moveable part 324 to maintain the position of the moveable part 324 when the cartridge is not received in the receiving portion 278.

The moveable part 324 may include an opening 326 therein to correspond and connect with the cartridge outlet. The opening 326 in the moveable part 324 may in fact define the carrier foam inlet 280. Alternatively, the cartridge outlet may be received under the moveable part with the carrier foam inlet positioned similarly under or below the moveable part.

The moveable part 324 preferably includes a concave surface 328 which corresponds to a shape of the expansion chamber of the cartridge.

The use of a moveable part 324 may have the result that a removable rear part 286, as described for the first embodiment, is not necessary, since the capsule can be inserted without removing part of the carrier body 276. However, it will be appreciated that a removable rear part may still be used if so required to enhance convenience of use.

The carrier body 276 preferably includes side walls 330 at or adjacent to the receiving portion 278. At least one of the side walls 330, and preferably both side walls 330, have an access opening 332 therein. The access openings 332 are elongate and are aligned with a longitudinal direction of the carrier body 276. The access openings 332 extend towards the movable part 324. This may allow for the cartridge, when received in the receiving portion 278, to be moved by the user's fingers towards the movable part 324, which permits release of the cartridge.

The access openings 332 are tapered, having a larger portion of the opening proximal to a rear part 286 or portion of the carrier body 276. The larger portion of the opening 332 being proximal to the rear part 286 allows for manual pressure to be more easily applied to the foam-generation elements so as to activate them and/or allows greater leverage to be applied to the cartridge from beneath to assist with removal.

It will be appreciated that the carrier body 276 may define a space, void or gap 334 open to the access openings 332 beneath the cartridge when received in the receiving portion 278. Such a space or gap 334 may be understood with respect to FIG. 13 which shows a curved portion 336 or seat where the second end of the mixing chamber may be received. It will be appreciated that the space or gap 334 may be defined below a line which extends from the seat or curved portion 336 to the carrier foam inlet 280. The gap or space 334 may assist with removal of the cartridge, for example allowing leverage to be applied underneath the cartridge. The second embodiment of the carrier 272 may be used in a similar or identical way as the first embodiment of the carrier 72 with the exception of insertion and removal of the cartridge, and the location of the application of manual pressure which is applied to the foam generation elements. The moveable part 324 is moved towards the carrier outlet 282, in the direction of block arrow A, to enlarge the receiving portion 278. The moveable part 324 may be moved via being pushed with the cartridge, for example. The cartridge is then positioned in the receiving portion 278 and the moveable part 324, under influence from the biasing means, moves towards its original position which may hold the cartridge in place.

The foam generation elements may be activated via applying manual pressure to the mixing chamber via the access openings 332. Foam is then generated and inhaled in the same or similar way as previously described.

After use, the cartridge can be moved towards the carrier outlet 282, via gripping the cartridge via the access openings 332, to move the moveable part 324 so as to enlarge the receiving portion 278. The cartridge can then be removed from the receiving portion 278, applying leverage to the cartridge via the gap 334 if required.

Although access openings are described, it will be appreciated that an upper wall or rib which defines the recess may not be included, and the opening may instead be a cut-away portion.

Although the second embodiment describes access openings and the moveable part, it will be appreciated that either or both features may be omitted.

It is therefore possible to provide a cartridge which produces a stable foam, as opposed to only a short-lived effervescence and/or a rapidly propelled inhalant, which allows for a user to consume or inhale a substance contained within the foam over a prolonged duration and with multiple inhalations. The cartridge is devoid of electrical energisation means/component and so reduces or eliminates a requirement for electrical charging.

It is therefore possible to provide a cartridge which produces a stable foam, as opposed to only a short-lived effervescence and/or a rapidly propelled inhalant, which allows for a user to consume or inhale a substance contained within the foam over a prolonged duration and with multiple inhalations. The cartridge is devoid of electrical energisation means/component and so reduces or eliminates a requirement for electrical charging.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

The embodiments described above are provided by way of examples only, and various other modifications will be apparent to persons skilled in the field without departing from the scope of the invention as defined herein.

The invention claimed is:

1. A stable-foam dispensing device to dispense a stable foam to a user via user suction over a prolonged duration, the dispensing device comprising:
    a foam-generating-component receiving portion for removably receiving a cartridge, wherein the stable-foam dispensing device further comprises the cartridge including stable-foam-generating components to generate the stable foam, said stable-foam-generating components together comprising a carbonate and an acid, the cartridge further including an openable barrier segregating at least one of the stable-foam-generating components from another of the stable-foam-generating components;
    an outlet to dispense the stable foam to the user;
    an expansion chamber fluidly coupled between the outlet and the stable-foam-generating components such that when the openable barrier is opened, the stable-foam-generating components interact to generate the stable foam, which is received by the expansion chamber before flowing to the outlet via a conduit to be consumed by the user via user suction over a prolonged duration; and
    wherein the foam-generating-component receiving portion includes a pointed protrusion configured to extend into the cartridge when the cartridge is received by the foam-generating-component receiving portion, wherein the pointed protrusion engages with the openable barrier to assist with dispensing at least one of said stable-foam-generating components to mix with the another of said stable-foam-generating components.

2. The stable-foam dispensing device as claimed in claim 1, wherein the cartridge includes a planar seal segregating at least one of the stable-foam-generating components from another of the stable-foam generating components.

3. The stable-foam dispensing device as claimed in claim 1, wherein the expansion chamber has a lower portion when in use under gravity, and wherein the conduit has an inlet opening positioned at the lower portion of the expansion chamber to receive stable foam from the lower portion of the expansion chamber.

4. The stable-foam dispensing device as claimed in claim 1, wherein the conduit has an inlet opening and a longitudinal extent which locates the inlet opening closer to the foam-generating-component receiving portion than to the outlet.

5. The stable-foam dispensing device as claimed in claim 1, wherein the conduit has an inlet opening, the conduit comprising a one-way valve therein to permit movement of foam from the inlet to the outlet and prevent or limit movement of fluid from the outlet to the inlet.

6. The stable-foam dispensing device as claimed in claim 1, wherein at least one of the carbonate and acid is a powder.

7. The stable-foam dispensing device as claimed in claim 1, wherein the openable barrier is configured to be opened by being broken.

8. The stable-foam dispensing device as claimed in claim 1, wherein one of the stable-foam-generating components comprises a stabiliser.

9. The stable-foam dispensing device as claimed in claim 1, wherein one of the stable-foam-generating components comprises a thickener.

10. The stable-foam dispensing device of claim 1, wherein the pointed protrusion extends axially to contact at least one of the stable-foam-generating components when the cartridge is received by the stable-foam-generating component receiving portion.

11. The stable-foam dispensing device of claim 1, wherein the stable-foam-generating component receiving portion includes a second pointed protrusion configured to extend into the cartridge when the cartridge is received by the foam-generating-component receiving portion.

12. The stable-foam dispensing device as claimed in claim 1, wherein the cartridge is a non-electrical dispensing cartridge.

13. The stable-foam dispensing device as claimed in claim 12, wherein one of the stable-foam-generating components comprises a liquid which is received in a chamber of the non-electrical dispensing cartridge.

14. The stable-foam dispensing device as claimed in claim 13, wherein the liquid is configured to be dispensed from the chamber via manual pressure applied to the chamber.

15. A method of increasing a duration of consumption activity, the method comprising the steps of:
   providing the device as claimed in claim 1;
   opening the openable barrier so that the stable-foam-generating components react to generate the stable foam which flows to the outlet via the expansion chamber and the conduit; and
   consuming the stable foam via user suction.

16. A stable-foam dispensing device to dispense a stable foam which comprises at least one of the following to be consumed by a user: nicotine, a component of *cannabis*, a medicine and/or dietary supplement, and a food or drink, the device comprising:
   a foam-generating-component receiving portion for removably receiving a non-electrical dispensing cartridge, wherein the stable-foam dispensing device further comprises the non-electrical dispensing cartridge having stable-foam-generating components to generate the stable foam, said stable-foam-generating components together comprising a carbonate and an acid, the non-electrical dispensing cartridge further including an openable barrier segregating at least one of the stable-foam-generating components from another of the stable-foam-generating components, wherein at least one of the stable-foam-generating components comprises at least one selected from the group consisting of the nicotine, the component of *cannabis*, the medicine and/or dietary supplement, and the food or drink;
   an outlet to dispense the stable foam to the user;
   an expansion chamber fluidly coupled between the outlet and the stable-foam-generating components such that when the openable barrier is opened, the stable-foam-generating components interact to generate the stable foam, which is received by the expansion chamber before flowing to the outlet via a conduit to be consumed by the user via user suction over a prolonged duration; and
   wherein the foam-generating-component receiving portion includes a pointed protrusion configured to extend into the non-electrical dispensing cartridge when the non-electrical dispensing cartridge is received by the foam-generating-component receiving portion, wherein the pointed protrusion engages with the openable barrier to assist with dispensing at least one of said stable-foam-generating components to mix with the another of said stable-foam-generating components.

17. The stable-foam dispensing device of claim 16, wherein the pointed protrusion extends axially to contact at least one of the stable-foam-generating components when the non-electrical dispensing cartridge is received by the foam-generating component receiving portion.

18. A dispensing apparatus to dispense a consumable to a user, the apparatus comprising:
   a component receiving container for removably receiving a cartridge, the component receiving container comprising a flexible material, wherein the dispensing apparatus further comprises the cartridge including components to generate the consumable, said components together comprising a carbonate and an acid, at least one of said components being received within a sub-container from which said at least one component is dispensable by pressure applied to the sub-container via flexion of the component receiving container;
   an outlet to dispense the consumable to the user;
   an expansion chamber fluidly coupled between the outlet and the components such that when said at least one component is dispensed from the sub-container, the components interact to generate the consumable, which is received by the expansion chamber before flowing to the outlet via a conduit to be consumed by the user via user suction; and
   wherein the component receiving container includes a pointed protrusion configured to extend into the cartridge when the cartridge is received by the component receiving container, wherein the pointed protrusion engages with the sub-container to assist with dispensing at least one of said components to mix with another of said components.

19. The dispensing apparatus of claim 18, wherein the pointed protrusion extends axially to contact at least one of the components when the cartridge is received by the component receiving container.

\* \* \* \* \*